United States Patent
Stewart

(10) Patent No.: US 9,757,155 B2
(45) Date of Patent: Sep. 12, 2017

(54) BONE INSTRUMENTATION COVER OR SHIELD

(76) Inventor: Kenneth Stewart, Bradenton, FL (US)

( * ) Notice: Subject to any disclaimer, the term of this patent is extended or adjusted under 35 U.S.C. 154(b) by 1145 days.

(21) Appl. No.: 13/236,180

(22) Filed: Sep. 19, 2011

(65) Prior Publication Data

US 2012/0022602 A1   Jan. 26, 2012

Related U.S. Application Data

(63) Continuation of application No. 10/634,368, filed on Aug. 6, 2003, now Pat. No. 8,025,685.

(51) Int. Cl.
*A61B 17/04* (2006.01)
*A61B 17/86* (2006.01)
*A61F 2/08* (2006.01)
*A61B 17/68* (2006.01)
*A61B 17/70* (2006.01)

(52) U.S. Cl.
CPC ........ *A61B 17/685* (2013.01); *A61B 17/7001* (2013.01)

(58) Field of Classification Search
None
See application file for complete search history.

(56) References Cited

U.S. PATENT DOCUMENTS

| | | |
|---|---|---|
| 177,749 A | 5/1876 | Redden |
| 194,655 A | 8/1877 | Cussen |
| 209,233 A | 10/1878 | Cox |
| 209,723 A | 11/1878 | Stowell |
| 211,224 A | 1/1879 | Cleary |
| 403,928 A | 5/1889 | Emeric |
| 467,129 A | 1/1892 | Cussen |
| 731,378 A | 6/1903 | Luther |
| 1,046,690 A | 12/1912 | Voelker |
| 1,221,473 A | 4/1917 | Riley |
| 1,368,864 A | 2/1921 | Turner |
| 1,495,389 A | 5/1924 | Heimerl et al. |
| 2,435,850 A * | 2/1948 | Siebrandt ............... 606/54 |
| 2,438,901 A | 4/1948 | Coxe |
| 2,447,561 A | 8/1948 | Brenner |
| 2,552,443 A | 5/1951 | Molinari |
| 2,704,846 A | 3/1955 | Weikert |
| 2,731,972 A | 1/1956 | Braun |
| 3,359,658 A | 12/1967 | Price |
| 3,638,789 A | 2/1972 | Tuszewski |
| 3,746,066 A | 7/1973 | McIntyre |

(Continued)

*Primary Examiner* — David Isabella
*Assistant Examiner* — Christine Nelson
(74) *Attorney, Agent, or Firm* — Barnes & Thornburg LLP

(57) ABSTRACT

A bone instrumentation cover or shield has a hollow cap or casing for encapsulating projecting parts of instrumentation installed in a bone, and a fastener portion for securing it to the bone or to parts of the instrumentation. The instrumentation shield or cover is made of medically safe material, in various sizes, and may be a rigid casing or pliable, stretchable, or adaptable with slidable, displaceable or pleated panels to provide a medically safe physical barrier between projecting parts of bone instrumentation constructs and surrounding bone and soft tissues, in order to minimize local irritation or injury and to provide a barrier to ingrowth from bone and/or fibrous tissues. The cap or casing is readily applied over the instrumentation, then cinched, tied or fastened to the instrumentation or adjacent areas.

22 Claims, 3 Drawing Sheets

(56) References Cited

U.S. PATENT DOCUMENTS

| | | | |
|---|---|---|---|
| 4,428,375 A * | 1/1984 | Ellman | 606/151 |
| 4,564,007 A | 1/1986 | Coombs et al. | |
| 4,683,596 A | 8/1987 | Cole | |
| 4,722,100 A | 2/1988 | Greer | |
| 4,815,640 A | 3/1989 | Johnson | |
| 4,820,305 A | 4/1989 | Harms et al. | |
| 4,864,695 A | 9/1989 | Gold | |
| 4,869,305 A | 9/1989 | Jones | |
| 4,918,839 A | 4/1990 | Brandon | |
| 5,050,999 A | 9/1991 | Van Loon, III | |
| 5,143,082 A * | 9/1992 | Kindberg | A61B 17/00234 128/DIG. 24 |
| 5,195,828 A | 3/1993 | Bush-Rodriquez | |
| 5,207,508 A | 5/1993 | Koutsis, Jr. | |
| 5,265,278 A | 11/1993 | Watanabe | |
| 5,279,539 A | 1/1994 | Bohan et al. | |
| 5,301,806 A | 4/1994 | Olson | |
| 5,411,165 A | 5/1995 | Ellis | |
| 5,518,313 A | 5/1996 | McAdam | |
| 5,653,337 A | 8/1997 | Cirigliano | |
| 5,662,649 A | 9/1997 | Huebner | |
| D453,620 S | 2/2002 | Vazquez | |
| D458,746 S | 6/2002 | Vazquez | |
| D460,616 S | 7/2002 | Vazquez | |
| 6,419,135 B1 | 7/2002 | Sali | |
| 6,436,136 B1 * | 8/2002 | Flodin | A61L 31/06 623/11.11 |
| 6,453,391 B2 | 9/2002 | Morita et al. | |
| 6,543,658 B2 | 4/2003 | Trevino | |
| D485,433 S | 1/2004 | Vazquez | |
| D488,297 S | 4/2004 | Vazquez | |
| 6,810,880 B1 * | 11/2004 | Jennings et al. | 128/849 |
| 7,069,597 B2 | 7/2006 | Hardenbrook | |
| 7,252,669 B1 | 8/2007 | McIntyre | |
| 2003/0163161 A1 | 8/2003 | Barron et al. | |

\* cited by examiner

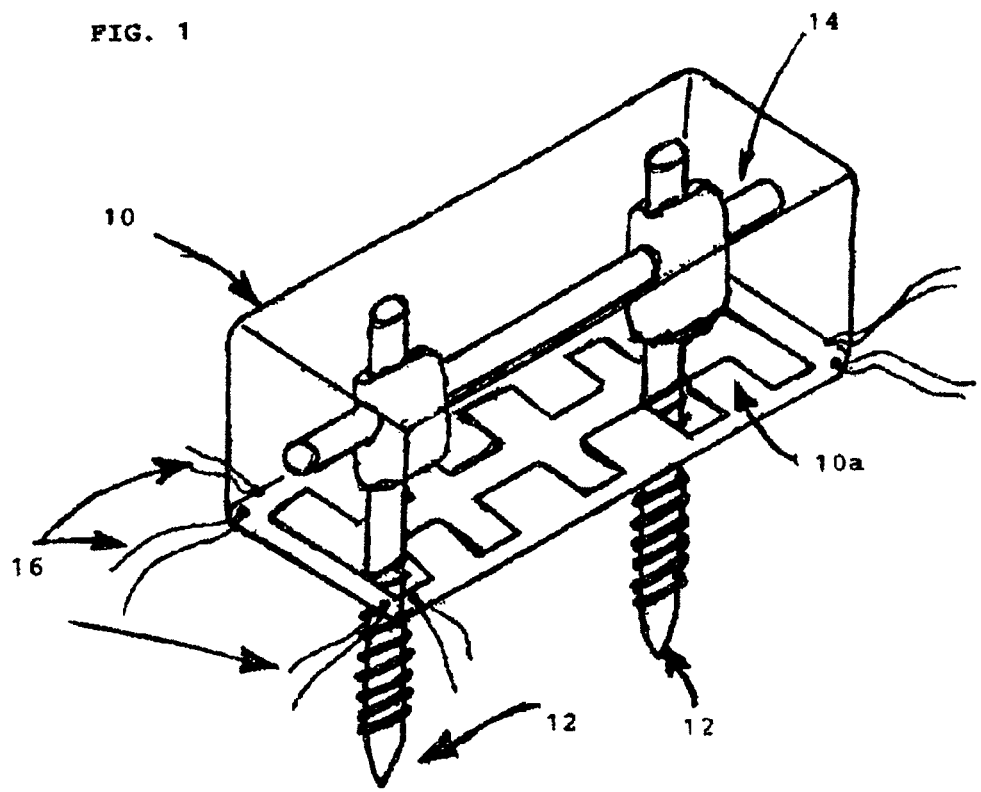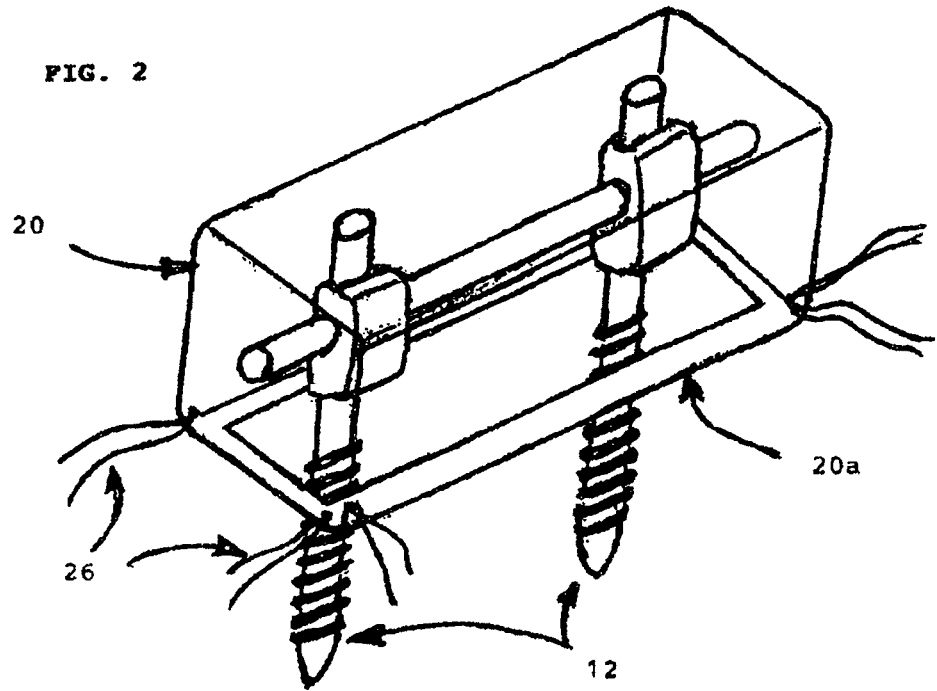

BONE INSTRUMENTATION COVER OR SHIELD

CROSS-REFERENCE TO RELATED APPLICATION

This United States Non-Provisional Patent Application is a Continuation Application of U.S. patent application Ser. 10/634,368, filed Aug. 6, 2003, entitled "Bone Instrumentation Cover or Shield," the disclosures of which are incorporated by reference in their entirety.

FIELD OF THE INVENTION

This invention generally relates to a device used in protect the body and the instrumentation installed in bone during spinal or reconstructive surgery, and particularly to a bone instrumentation cover or shield.

BACKGROUND OF INVENTION

Spinal bone deterioration, disc rupture, degenerative disc disease or deformity is surgically correctable by installing a rod secured to pedicle screws mounted into good bone in order to support or reinforce the deteriorated, weakened, or deformed area.

However, the presence of instrumentation installed in bone can present problems for the patient. Projecting parts of the instrumentation can irritate and cause swelling or injury to the surrounding tissues. Ingrowth of bone or fibrous tissue into parts of the instrumentation is possible if the bone or tissue regenerates, causing possible interference with the function of the instrumentation or perhaps making it difficult to later remove the instrumentation if it is no longer needed or if a next progressive stage of instrumentation is required. Many of the systems in use tend to be fairly bulky and frequently lead to problems within patients. Bursae may form which can lead to pain and possible skin necrosis and breakdown. Removing the instrumentation may ultimately be necessary in such cases. It is therefore desirable to provide a way to protect the body and the instrumentation installed in bone during spinal or reconstructive surgery.

SUMMARY OF INVENTION

In accordance with the present invention, a bone instrumentation cover or shield comprises a cap or casing which is dimensioned to be placed over and to encapsulate projecting parts of instrumentation installed in a bone, and a fastener portion provided at a lower edge of the cap or casing for securing it to the bone or to parts of the instrumentation where it is installed in the bone. The cap or casing is shaped and dimensioned to fit over the projecting parts of the instrumentation. The fastener portion is designed to attach and hold the cap or casing to the bone or to parts of the instrumentation installed in the bone.

In one preferred embodiment, the cover or shield is formed with a hollow cap or casing in a suitable shape such as a three-dimensional oval or parallelpiped for fitting over the projecting parts of the instrumentation, and has a lower frame with a toothed-edge bottom for locking on to the parts of the instrumentation that are mounted into the bone (pedicle screws). The fastener can include pre-loaded sutures for attachment to the bone or to adjacent parts of the instrumentation.

In another preferred embodiment, the cover or shield is formed with a hollow cap or casing as described above, and a lower frame is provided with an aperture to accommodate parts of the instrumentation that extend there from to where they are mounted into or fastened to the bone.

In a further embodiment, the cap or casing is formed as a pliable or flexible pouch, and the fastener portion is formed by one or more drawstrings for cinching the lower edge of the pouch opening around the parts of the instrumentation mounted into or fastened to the bone. The extra lengths of the drawstrings may be fastened to the bone or instrumentation like the sutures described above.

In yet another embodiment, the cap or casing is formed as a pliable or flexible sheath, and the fastener portion is formed by a lower cinch ring having openings therein for threading through a number of suture strings for tightening the cap vertically down to the cinch ring over the instrumentation, and one or more drawstrings in the cinch ring for tightening horizontally around the instrumentation.

In still another embodiment, the cap or casing is formed with slidable or displaceable panels or with pleats, for adjustment of its length, width, or height snugly around the instrumentation.

Other objects, features, and advantages of the present invention will be explained in the following detailed description of the invention having reference to the appended drawings.

BRIEF DESCRIPTION OF DRAWINGS

FIG. 1 is a schematic drawing of a first embodiment of the invention having a cover or shield formed with a hollow cap or casing and a lower frame with a toothed-edge bottom for locking on to instrumentation mounted into the bone.

FIG. 2 is a schematic drawing of a second embodiment in which the cover or shield is formed with a hollow cap or casing and a lower frame with an aperture for the instrumentation.

DETAILED DESCRIPTION OF INVENTION

Figure 3A:
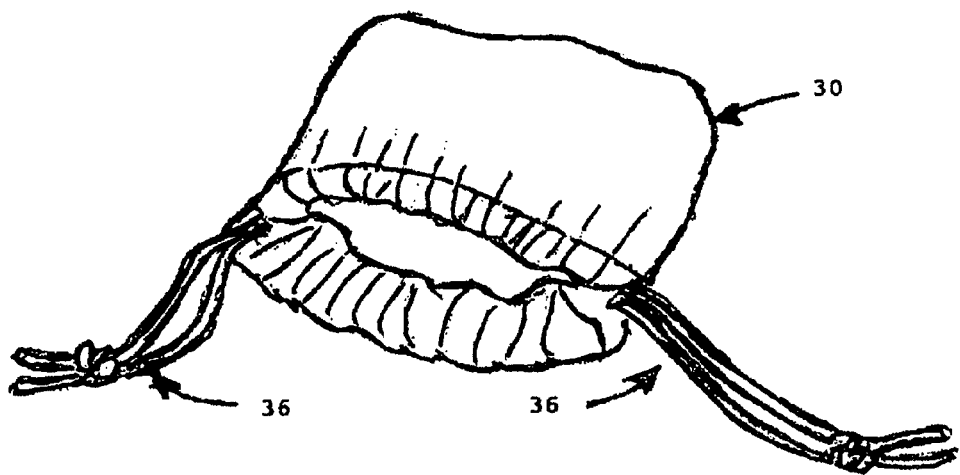
FIGS. 3A and 3B are schematic drawings of a third embodiment in which the cover or shield is a pliable or flexible pouch, and the fastener portion has drawstrings for cinching around the instrumentation.

Referring to FIG. 1, a first embodiment of the instrumentation cover or shield in accordance with the present invention is formed with a hollow cap or casing 10 and a lower frame 10a formed with a toothed-edge bottom for locking onto instrumentation, i.e., pedicle screws 12 having screw-threaded lower portions which are mounted into the bone or bones of the patient. A rod 14 is secured through the post portions of the pedicles 12 to provide rigid instrumentation support across a given area of the bone. When the instrumentation has been mounted into the bone in a surgical procedure, the parts projecting above the bone can cause irritation of injury to surrounding bones or tissues. The cover casing 10 is designed and dimensioned to encapsulate the projecting parts to prevent irritation or injury. The cover is applied from the dorsal aspect, inserting the longitudinal rod and pedicle screw ends through the mid-line aperture, then using the toothed edges of the lower frame 10a to lock onto the lower parts of the pedicle screw 12 adjacent where they enter the bone. The toothed edge has teeth spacings for locking onto the projecting stems of the pedicle screw. Sutures 16 may also be pre-loaded at manufacture or attached to openings around the edge of the frame 10a to allow fastening of the cover to the adjacent bone or tissue or instrumentation construct.

The instrumentation cover is designed to cover any spinal or other bone instrumentation installed in the body. The cover can be used for pedicle screw/rod constructs, pedicle screw/plates, bone anchors, or hook and rod constructs, such as are commonly used for cervical, lumbar, or thoracic spinal instrumentation. The shield or cover is made of proven, medically safe material, such as GoreTex,™ Dacron,™ polyurethane, or any other safe, implantable material. The cover may be intended to be permanently installed, or may be removable in a subsequent surgical procedure. The shield or cover preferably is in the form of a solid rectangle or solid oval or other suitable shape and closely fits onto the instrumentation in a manner analogous to an armrest cover on the arm of a chair. It can be made in different sizes or shapes for one-level, two-level, or multi-level instrumentation, and may also be adjustable in size (see further embodiments described below). The shield or cover prevents ingrowth of bone or fibrous tissue into interstices of the instrumentation because it provides a mechanical barrier to such intrusion. If the cover needs to be removed, such as when the instrumentation is to be adjusted, replaced, or removed, it is removed in a similar surgical procedure where it is accessed through an incision and its lower frame and/or sutures or other fasteners are removed to expose the instrumentation.

The instrumentation cover may also be made from a molded material, such as polyurethane foam, or a moldable material such as a non-toxic putty, or from a pliable or stretchable material as long as it is safe for implantation. The cover is designed to fit or to be adjusted around the instrumentation so that it covers it snugly and dislodgement or displacement is precluded. The cover is typically installed immediately after placement of the instrumentation. Permanent sutures may be used, or absorbable, biodegradable sutures may be used to initially hold the cover in place until healing of the soft tissue surrounding the cover. The instrumentation cover may also be made of a hardenable or gelable material such as polycarbonate urethane, elastomeric material, or polyurethane foam, which can cure in situ and has well-established biochemical compatibility with excellent mechanical strength and elastic properties.

Another possible material for the cover is a hydrogel or "bioglue" which is composed of bovine albumin and glutaaldehyde. This has been used as a chemical adhesive and can be applied around the instrumentation using a two-chambered cartridge stored at room temperature. It can be injected into a form placed over the instrumentation and solidified to 90% solid within 30 seconds, and completely in two minutes, without generation of heat.

In FIG. 2, a second embodiment of the invention is shown in which the cover or shield is formed with a hollow cap or casing 20, similar to the one described previously, and a lower frame 20a with an open box-like aperture for accommodating different configurations or sizes of instrumentation (here again, pedicle screws 12). Sutures 26 are anchored to small openings around the edges of the lower frame and used to hold the cover in place by attachment to adjacent bone areas or tissue.

Figure 3B:
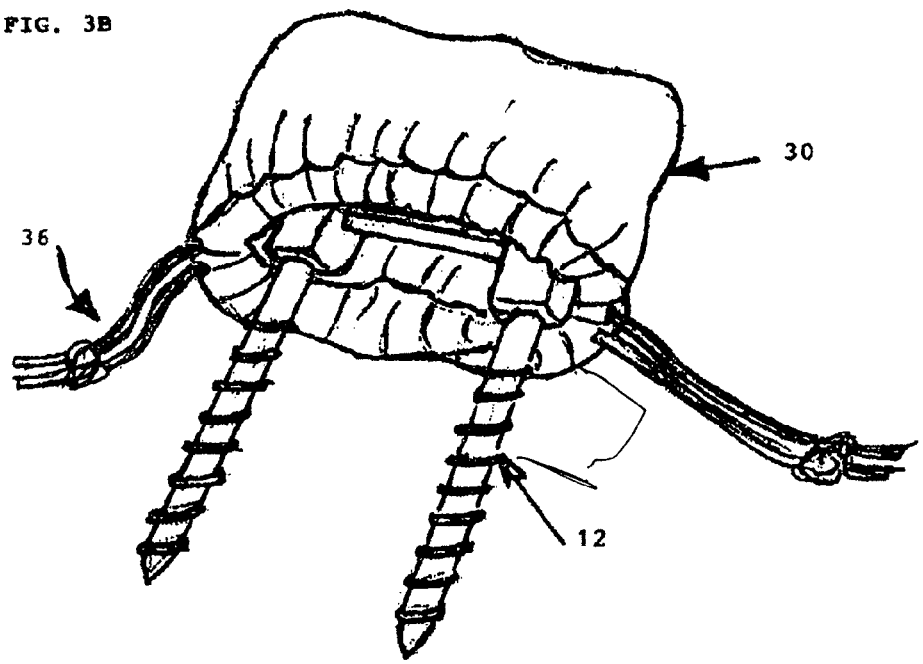

In FIGS. 3A and 3B, a third embodiment of the cover or shield is formed as a pliable or flexible pouch 30 with drawstrings 36 for tightening the pouch down onto the instrumentation and cinching it around the parts of the instrumentation (here again, pedicle screws 12) to hold it in place. The ends of the drawstrings may be wrapped around the instrumentation construct or tied to adjacent bone areas or tissue or instrumentation construct.

Figure 4:
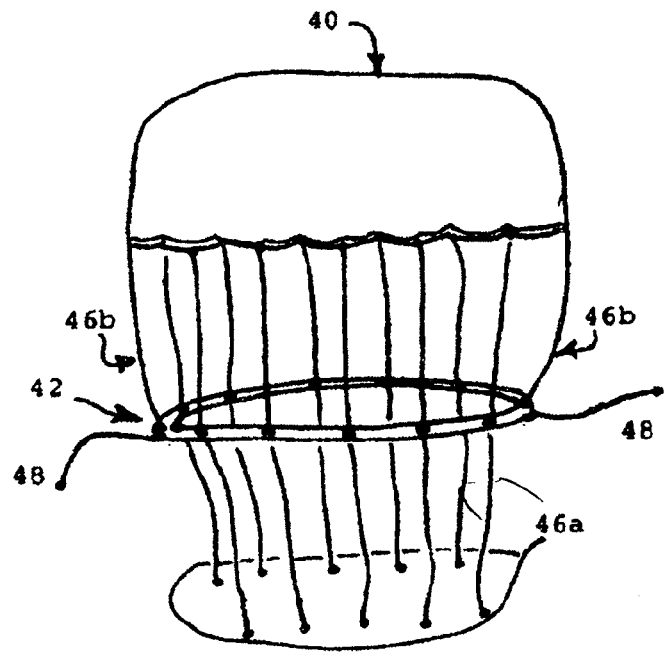
FIG. 4 is a schematic drawing of a fourth embodiment in which the cover or shield is formed with a cap, and the fastener portion is formed by a lower cinch ring threaded with a number of suture strings for tightening the cap vertically down to the cinch ring, and drawstrings for tightening the cinch ring horizontally around the instrumentation.

In FIG. 4, a fourth embodiment of the cover or shield is formed with a pliable or flexible cap or sheath 40 for encapsulating the instrumentation, and a lower cinch ring 42 for tightening the cap down around the instrumentation. The cinch ring has openings 42a through which a number of adjustable suture strings 46a tied to the lower edge of the cap portion 40 are threaded. The cinch ring 42 and cap portion 40 are deployed over the instrumentation, and then the loose ends of the adjustable suture strings are pulled through the cinch ring openings 42a to tighten the cap vertically down onto the instrumentation. Two suture strings 46b on opposite sides of the cap have ends that are attached to the cinch ring and are not adjustable, as their function is to tie the cinch ring to the cap portion so that it does not slip away from the cap and adjustable sutures while being handled. The cinch ring is in tubular form and is made of a flexible material, such as a synthetic fabric, so that it can also be cinched circumferentially (horizontally) around the lower parts of the instrumentation adjacent the bone, using drawstrings 48. The suture string and drawstring ends may be trimmed and tied off to the cinch ring or instrumentation construct to prevent accidental removal.

Figure 5:
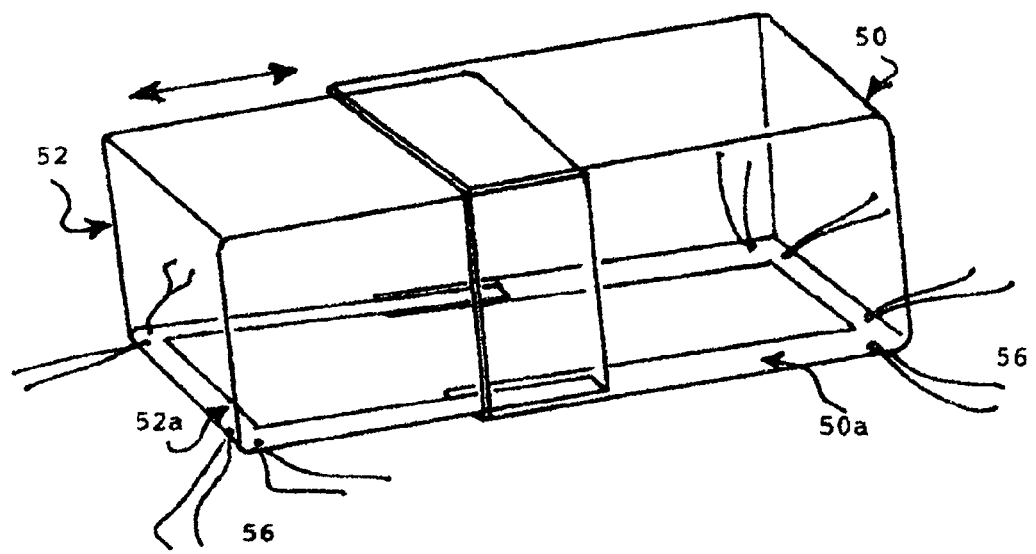
FIG. 5 is a schematic drawing of a fifth embodiment in which the cover or shield has slidable or displaceable panels for adjustment of its length, width, or height around the instrumentation.

In FIG. 5, a fifth embodiment of the cover or shield has a casing formed with slidable or displaceable parts or panels 50, 52 for adjustment of its length around the instrumentation (in the direction of the bidirectional arrow in the figure). Alternatively, the panels may be formed with pleated parts for making the dimensional adjustment. The panels may similarly be made adjustable in width or height. Sutures 56 attached to the lower frame parts 50a, 52a are used to fasten the cover to the instrumentation and/or adjacent bone areas or tissue.

In summary, the bone instrumentation shield or cover is designed to provide a medically safe physical barrier for implantation between projecting parts of bone instrumentation constructs and surrounding bone and soft tissues. The shield or cover minimizes local irritation or injury to soft tissues from the instrumentation and also serves as a barrier to ingrowth from bone and/or fibrous tissues. It can be formed in a variety of forms, from solid casing, to semi-pliable sheath-like structure, to soft pouch or cinch sack. With or without cross clips in place, the cover can be readily applied from the dorsal aspect over the instrumentation, then cinched, tied or fastened to the instrumentation adjacent where it enters the bone or to the adjacent bone area of tissue, using suture ties, suture strings, drawstrings and the like. The cover is made of medically safe material, and can come in various sizes or constructed to be pliable, stretchable, or adaptable with slidable, displaceable or pleated panels. A variety of dimensional arrangements may be made for single-level, two-level, three-level and long, multilevel instrumentation constructs.

It is understood that many modifications and variations may be devised given the above description of the principles of the invention. It is intended that all such modifications and variations be considered as within the spirit and scope of this invention, as defined in the following claims.

The invention claimed is:

1. A bone instrumentation cover installed over bone instrumentation adapted to project from the bone of an animal during bone repair or reconstruction surgical procedure on the animal, the bone instrumentation cover comprising:
   a hollow cap sized for encapsulating a part of a bone instrumentation which has been installed in bone, the hollow cap adapted for placement in the body of the animal and for encapsulating a part of the bone instrumentation which projects from the bone, the hollow cap providing a medically safe physical barrier between the part of the bone instrumentation and the surrounding bone and soft tissue in the animal, the hollow cap being adapted to separate the part of the bone instrumentation from substantially all of the surrounding soft tissue so that the hollow cap prevents ingrowth of substantially all of the surrounding soft tissue through the cap into the bone instrumentation which projects from the bone, and
   the hollow cap having a fastener portion securing the cap to the bone instrumentation portion which projects from the bone.

2. A bone instrumentation cover or shield according to claim 1, wherein the fastener portion includes:
   a cinch ring which is not a part of said hollow cap, and said cinch ring having one or more draw strings for tightening the hollow cap circumferentially around the instrumentation during said bone repair or reconstruction surgical procedure, and
   a suture string for securing the hollow cap to one of adjacent bone and adjacent tissue.

3. A bone instrumentation cover according to claim 2, further including a plurality of first suture strings, each first suture string having a first end and a second end, the first ends of the first suture strings being fixedly connected to the hollow cap, and the second ends of the first suture strings are threaded through the cinch ring for tightening the hollow cap to the cinch ring with the hollow cap extending over the bone instrumentation installed during the bone repair or reconstruction surgical procedure.

4. A bone instrumentation cover according to claim 3, further including a second suture string with a first end of the second suture string coupled to an edge of the cap and with a second end of the second suture string coupled to the cinch ring.

5. A bone instrumentation cover according to claim 4, further including an additional second suture string with a first end of the additional second suture string coupled to an edge of the cap and with a second end of the additional second suture string attached to the cinch ring.

6. A bone instrumentation cover according to claim 1, wherein the hollow cap is adjustable in size and is adapted for removal in a subsequent surgical procedure.

7. A bone instrumentation cover according to claim 1, wherein the hollow cap is adapted to encapsulate substantially all of the bone instrumentation adapted to project from the bone after an initial surgical procedure and is removable in a subsequent surgical procedure.

8. A bone instrumentation cover according to claim 1, wherein the hollow cap includes pleats adapted for adjustment of one of the length, width and height of the hollow cap so that the hollow cap fits snugly around the bone instrumentation.

9. A bone instrumentation cover according to claim 1, wherein the fastener portion includes a lower frame of the hollow cap provided with an open, box-like aperture shaped for locking the cap to the bone instrumentation.

10. A bone instrumentation cover according to claim 1, wherein the hollow cap is made of a medically safe material consisting of polyurethane.

11. The combination of claim 1, wherein the hollow cap comprises hydrogel.

12. The bone instrumentation cover of claim 1, wherein the fastener portion comprises biodegradable sutures.

13. A bone instrumentation cover installed over bone instrumentation adapted to project from the bone of an animal during bone repair or reconstruction surgical procedure, the bone instrumentation cover comprising:
   a hollow cap shaped to encapsulate a part of a pedicle screw capable of being installed in bone in the body of a human, the hollow cap being shaped to encapsulate a part of the pedicle screw which projects from the bone and is in the body of the human, the hollow cap being adapted for placement in the body of the human during surgery, the hollow cap being adapted to separate the part of the pedicle screw capable of projecting from the bone in the body of the human from surrounding bone and soft tissue, the hollow cap separating the part of the pedicle screw from substantially all of the surrounding soft tissue so that during healing the hollow cap prevents ingrowth of bone or tissue through the cap into the part of the pedicle screw which projects from the bone, and
   a fastener snugly securing the cap to the pedicle screw.

14. A bone instrumentation cover according to claim 13, further including sutures that are absorbable in vivo and secure the hollow cap to one of adjacent bone and adjacent tissue.

15. A bone instrumentation cover according to claim 14, wherein the sutures include a plurality of adjustable suture strings, each adjustable suture string having a first end and a second end, the first ends of the adjustable suture strings being fixedly connected to the hollow cap, and the second ends of the adjustable suture strings are a cinch ring tightening the hollow cap to the cinch ring with the hollow cap extending over the pedicle screw installed during the bone repair or reconstruction surgical procedure.

16. A bone instrumentation cover according to claim 15, further including a non-adjustable suture string with a first end of the non-adjustable suture string tied to a lower edge of the cap and with a second end of the non-adjustable suture string attached to the cinch ring.

17. A bone instrumentation cover according to claim 15, wherein the cinch ring has openings therein, said cinch ring not being a part of said hollow cap, and said cinch ring being a tubular form.

18. A bone instrumentation cover according to claim 13, wherein the hollow cap is made of a medically safe material consisting of polyurethane.

19. The combination of a bone implant and a barrier comprising:
   a bone implant capable of extending from the bone of an animal, and
   a barrier material adapted for snugly covering only the portion of the bone implant in the animal which projects from the bone and separating the bone implant from substantially all of the surrounding soft tissue, wherein the barrier material is a medically safe physical barrier between the portion of the part of the bone implant that is covered and the surrounding soft tissue of the animal and wherein the barrier material prevents ingrowth during healing of substantially all of the surrounding tissue into the bone implant, and means for fastening the barrier material to the bone implant.

20. The combination of claim 19, wherein the bone implant is a pedicle screw.

21. The combination of claim 19, wherein the barrier material is designed to be adjusted around the portion of the bone implant which projects from the bone so that it snugly covers the portion of the bone implant which projects from the bone.

22. The combination of claim 19, wherein the barrier material is hydrogel.

* * * * *